(12) United States Patent
Kim et al.

(10) Patent No.: US 6,648,814 B2
(45) Date of Patent: Nov. 18, 2003

(54) MICRO-ROBOT FOR COLONOSCOPE WITH MOTOR LOCOMOTION AND SYSTEM FOR COLONOSCOPE USING THE SAME

(75) Inventors: Byungkyu Kim, Seoul (KR); Young Mo Lim, Yongin Kyunggi-do (KR); Young Jae Lee, Incheon (KR); Yeh-Sun Hong, Seoul (KR); Soo Hyun Kim, Taejon (KR); Jong-Oh Park, Seoul (KR)

(73) Assignee: Korean Institute of Science and Technology, Seoul (KR)

( * ) Notice: Subject to any disclaimer, the term of this patent is extended or adjusted under 35 U.S.C. 154(b) by 0 days.

(21) Appl. No.: 09/993,851

(22) Filed: Nov. 14, 2001

(65) Prior Publication Data

US 2002/0156347 A1 Oct. 24, 2002

(30) Foreign Application Priority Data

Apr. 24, 2001 (KR) ........................................ 2001-22141

(51) Int. Cl.[7] ................................................ A61B 1/01
(52) U.S. Cl. ...................... 600/114; 378/60; 356/241.6; 604/95.03
(58) Field of Search ................................ 600/150, 151, 600/114, 115, 117, 141; 104/138.2; 318/82–85; 378/60; 356/241.6; 604/95.03

(56) References Cited

U.S. PATENT DOCUMENTS

| | | | |
|---|---|---|---|
| 4,148,307 A | | 4/1979 | Utsugi |
| 4,176,662 A | | 12/1979 | Frazer |
| 4,207,872 A | | 6/1980 | Meiri et al. |
| 4,389,208 A | | 6/1983 | LeVeen et al. |
| 5,018,509 A | * | 5/1991 | Suzuki et al. ............... 600/115 |
| 5,031,510 A | * | 7/1991 | Krauter ......................... 92/92 |
| 5,090,259 A | * | 2/1992 | Shishido et al. ........... 73/866.5 |
| 5,337,732 A | | 8/1994 | Grundfest et al. |
| 5,398,670 A | * | 3/1995 | Ortiz et al. ................. 600/114 |
| 5,662,587 A | | 9/1997 | Grundfest et al. |
| 5,906,591 A | | 5/1999 | Dario et al. |
| 6,162,171 A | | 12/2000 | Ng et al. |

FOREIGN PATENT DOCUMENTS

JP 6-206538 * 7/1994 ........... B61B/13/10

* cited by examiner

*Primary Examiner*—John Mulcahy
(74) *Attorney, Agent, or Firm*—Jaeckle Fleischmann & Mugel, LLP

(57) ABSTRACT

A micro-robot for colonoscope with motor locomotion comprises an information detecting unit for obtaining information of the interior of the colon and a driving unit for generating its own locomotion and moving the information detecting unit without causing any damages to the walls of the colon.

19 Claims, 12 Drawing Sheets

MICRO-ROBOT FOR COLONOSCOPE WITH MOTOR LOCOMOTION AND SYSTEM FOR COLONOSCOPE USING THE SAME

CROSS-REFERENCE TO RELATED APPLICATIONS

This application claims the benefit of Korean Patent Application Serial No. 2001-22141, filed Apr. 24, 2001.

BACKGROUND OF THE INVENTION

1. Field of the Invention

The invention relates to a micro-robot for inspecting and examining the interior of the colon, and particularly, to a micro-robot for colonoscope with motor locomotion which is capable of generating its own driving force and flexibly moving in the colon without causing any damages to the inner wall of the colon, and a system for colonoscope using the micro-robot.

2. Background of the Invention

Nowadays, most of micro-robots for colonoscope have been designed for moving like inchworm, which moves in the colon with one contraction/extension module at the center and two clamping modules at front and rear ends and obtains information (for example, images) of the walls. Here, the inchworm-like motion of the micro-robot does not make it freely and flexibly move in the colon. Particularly, in a problematic colon or a very angulated region the micro-robot does not easily advance and pass. It possibly happens to rupture the walls as a result of the repeated clamping operations that the micro-robot tries to pass the region of the colon. Even though it passes the region, the walls are significantly damaged thereon due to the clamping that is one of main procedures to implement the inchworm-like motion.

In addition to the shortcomings above, the inchworm-type micro-robot have the shortcomings that an endoscopist or a physician performs the inspection or examination of the intestine to obtains a precise information identifying between the damages made by inchworm-type endoscope and the diseases already existing for a long time and thereby a patient suffers from the operation during the time.

BRIEF SUMMARY OF THE INVENTION

The object of the present invention is to provide a micro-robot for colonoscope which is capable of flexibly moving in the colon without causing any damages to the walls by its own locomotion and obtaining the precise information of the walls regardless of the colon loops, and a system for colonoscope using the micro-robot.

The another object of the present invention is to provide a micro-robot for colonoscope which is capable of flexibly and freely moving in the colon without causing any damages to the walls by its own locomotion which is generated by motors, being steered in its advancing direction by linear actuators together with the wheels driven by the locomotion from the motor, and obtaining the precise information of the walls regardless of the colon loops and a system for colonoscope using the micro-robot.

For the object above according to the present invention, there is provided a micro-robot for colonoscope with motor locomotion which comprises an information detecting unit for obtaining information of the interior of the colon; and a driving unit for generating its own locomotion and moving the information detecting unit without causing any damages to the walls of the colon.

For another object above according to the present invention, there is provided a system for colonoscope using the micro-robot, wherein said system comprising: a micro-robot for obtaining information of the interior of the colon; a controlling unit for controlling the micro-robot; and a power supplying unit for supplying power to the microrobot and the controlling unit.

DETAILED DESCRIPTION OF THE INVENTION

Figure 1:
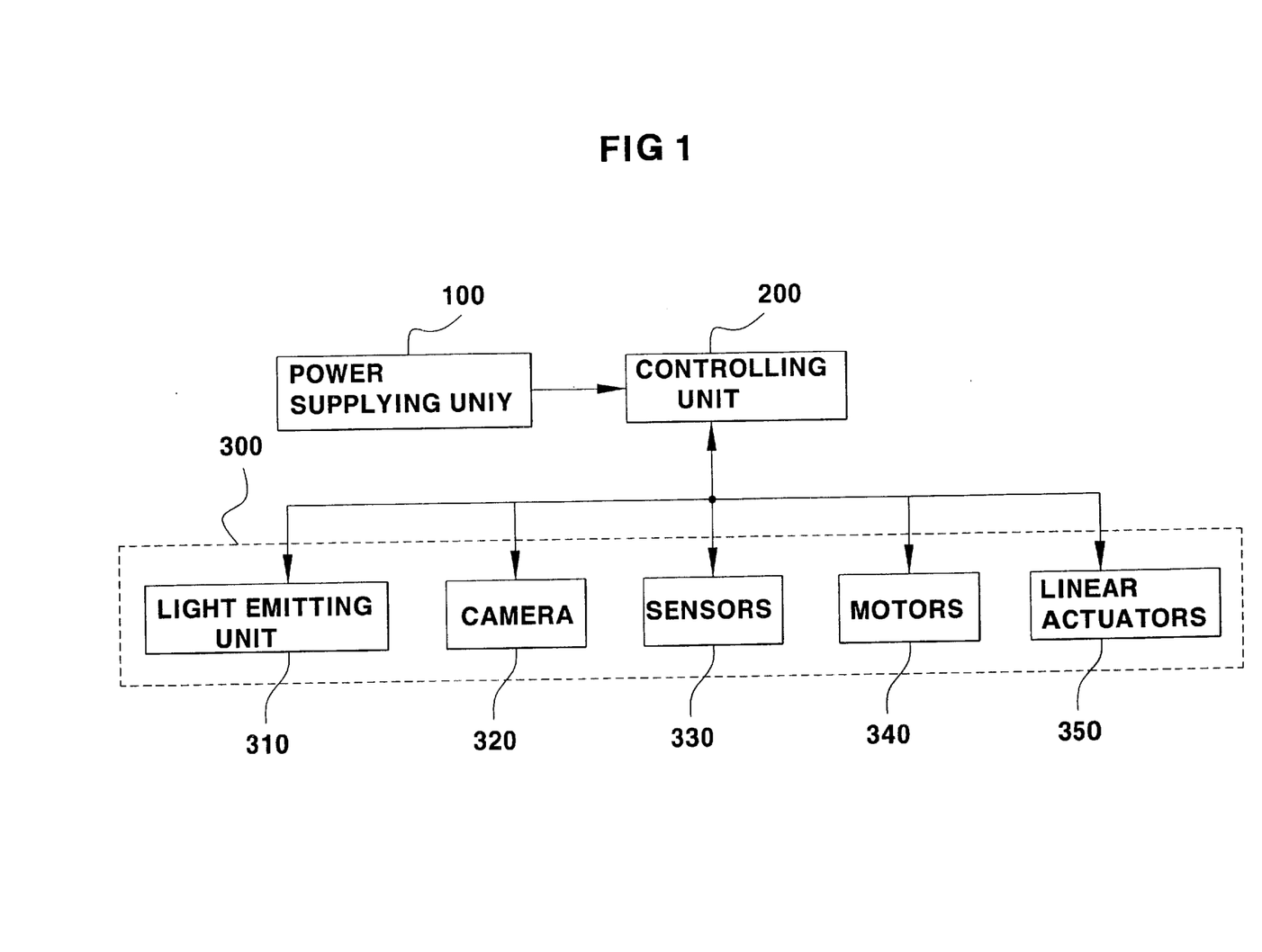
FIG. 1 is a schematic block diagram illustrating a colonoscope system using a micro-robot for colonoscope with motor locomotion in accordance with the present invention.

FIG. 1 is a schematic block diagram illustrating a colonoscope system using a micro-robot for colonoscope with motor locomotion in accordance with the present invention.

As shown in the drawing, the micro-robot for colonoscope with motor locomotion comprises a micro robot 300 to move in the colon and obtain information (for example, images) of the colon, a controlling unit 200 to control the micro-robot 300, and a power supplying unit 100 to supply power to the controlling unit 200 and the micro-robot 300.

The micro-robot 300 includes a light emitting unit 310 (for example, a light emitting diode (LED)) to light the interior of the colon, a camera 320 to take images of the interior as the light emitting unit 310 lighten, sensors 330 (for example, a tactile sensor) to detect the force or the pressure which micro-robot apply to the inner walls of colon, motors 340 to generate its driving forces or locomotion, and linear actuators 350 to change the advancing direction of the micro-robot 300 as their lengths vary.

Figure 2:
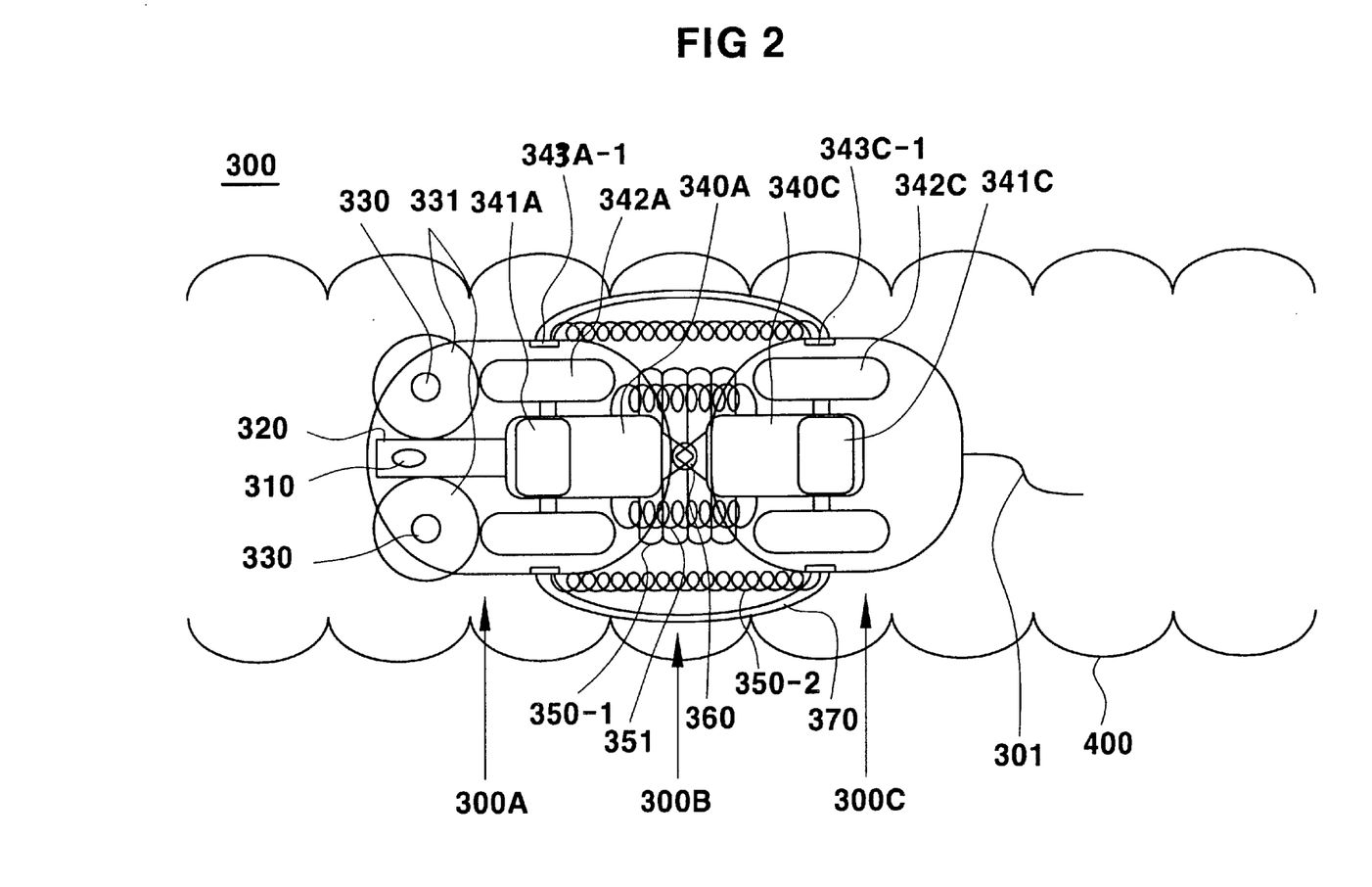
FIG. 2 is perspective view illustrating a micro-robot for colonoscope with motor locomotion in accordance with the first embodiment of the present invention.

FIG. 2 is a perspective view illustrating a micro-robot for colonoscope with motor locomotion of FIG. 1 in accordance with the first embodiment of the present invention.

As shown in the drawing, the micro-robot 300 comprises a front driving unit 300A which includes a light emitting unit 310 to illuminate the interior of the colon, a camera 320 to take images of the colon interior, sensors 330 to detect the pressure or the force which micro-robot applies to the inner wall of colon as the micro-robot 300 advances in the colon, passive steering units 331 to help the micro-robot 300 to advance in the colon by rotating themselves with reference to their own shafts and to include the sensors 300 therein, a motor 340A to generate a driving force or locomotion, a plurality of wheels 342A-1 and 342A-2 to carry the micro-robot 300 according to the driving force and locomotion, and a driving force transmission unit 341A to transmit the driving force or locomotion from the motor 340A to the wheels 342A-1 and 342A-2; a rear driving unit 300C which includes a motor 340C to generate a driving force or locomotion corresponding to the movement of the front driving unit 300A, a plurality of wheels 342C-1 and 342C-2 to carry the micro-robot 300 according to the driving force or locomotion, and a driving force transmission unit 341C to transmit the driving force or locomotion from the motor 340C to the wheels 342C-1 and 342C-2, here the front driving unit 300A and the rear driving unit 300C are aligned within a predetermined interval; a supporting unit 370 connected the front and rear driving unit 300A and 300C forming the body of the micro-robot 300 and fixing the micro-robot 300 to the wall of the colon, wherein the ends of the supporting unit 370 is slidably fixing to sliding units 343A-1 and 341C-1 of the front and rear driving unit 300A and 300C, respectively; fixing linear actuators 350-2 to fix the supporting unit 370 to the inner walls by relatively increasing the width of the body, which is achieved by the contraction of the fixing linear actuator 350-2; and a steering unit 300B to connect the front and rear driving unit 300A and 300C and control them to change the advancing direction of the micro-robot 300.

Here, the fixing linear actuators 350-2 in accordance with the present invention are embodied by pneumatic pressure cylinder operated by air pressure or shape memory alloy and polymer varying its length according to the variation of the supplied power. In addition, the micro-robot 300 is connected to a external device such as the controlling unit 200 and power supplying unit 100 via a wire 301 which further comprises electrical wires and/or a hose to flow air.

Figure 3:
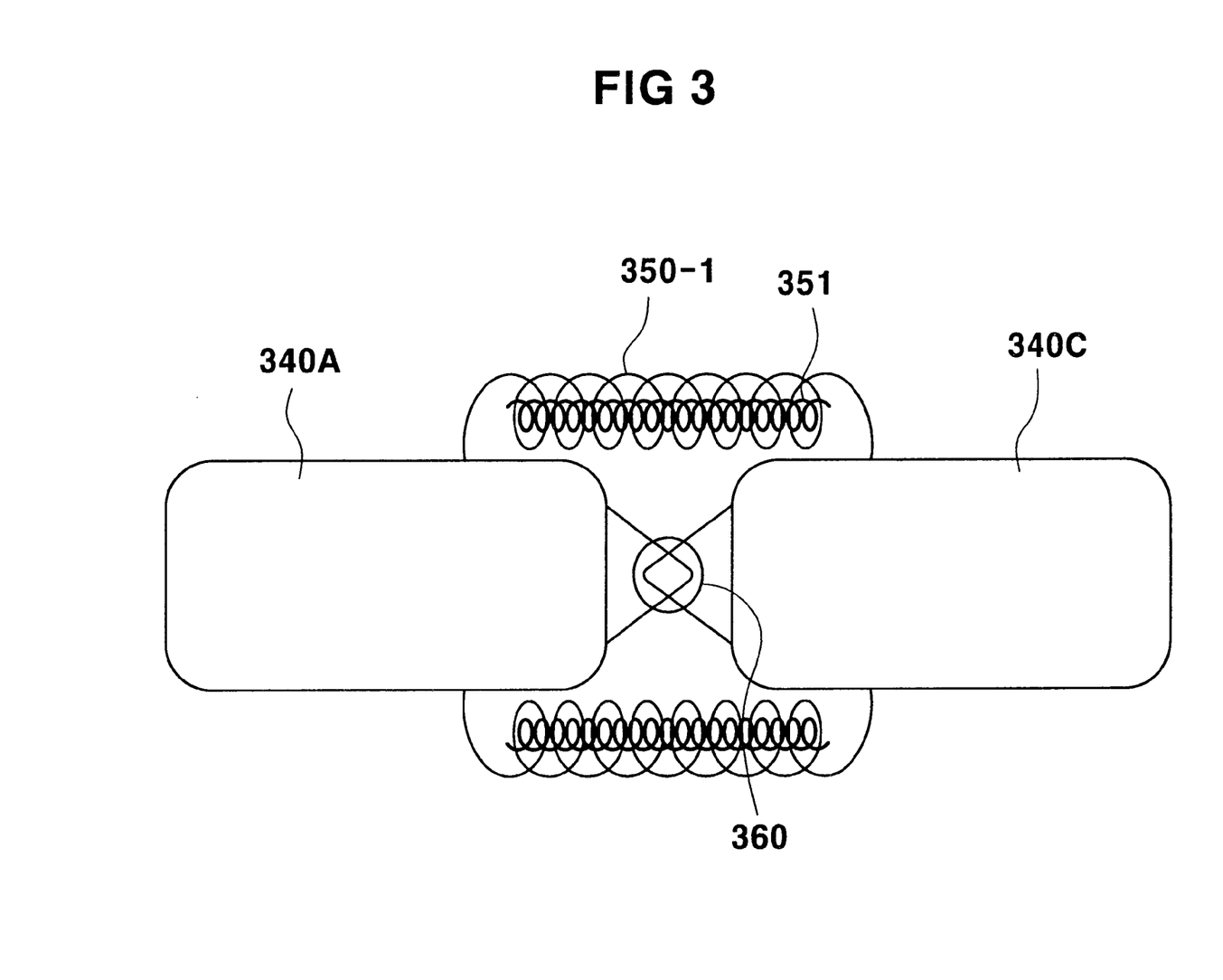
FIG. 3 shows a steering unit of the micro-robot for colonoscope with motor locomotion of FIG. 2.

FIG. 3 shows a steering unit of the micro-robot for colonoscope with motor locomotion of FIG. 2.

As shown in the drawing, the steering unit 300B of the micro-robot 300 comprises a revolute joint 360 to relatively rotate the front driving unit 300A and the rear driving unit 300C each other according to the operation of the steering linear actuators 350-1, steering linear actuators 350-1 to control the steering angle of the front driving unit 300A and the rear driving unit 300C with reference to the revolute joint 360, spring 351 to maintain a predetermined interval between the front driving unit 300A and the rear driving unit 300C and to align them in a straight line provided that the linear actuators 350-1 do not operate.

Here, the steering linear actuators 350-1 in accordance with the present invention are embodied by pneumatic pressure cylinder operated by air pressure or shape memory alloy and polymer varying its length according to the variation of the supplied power.

Figure 4:
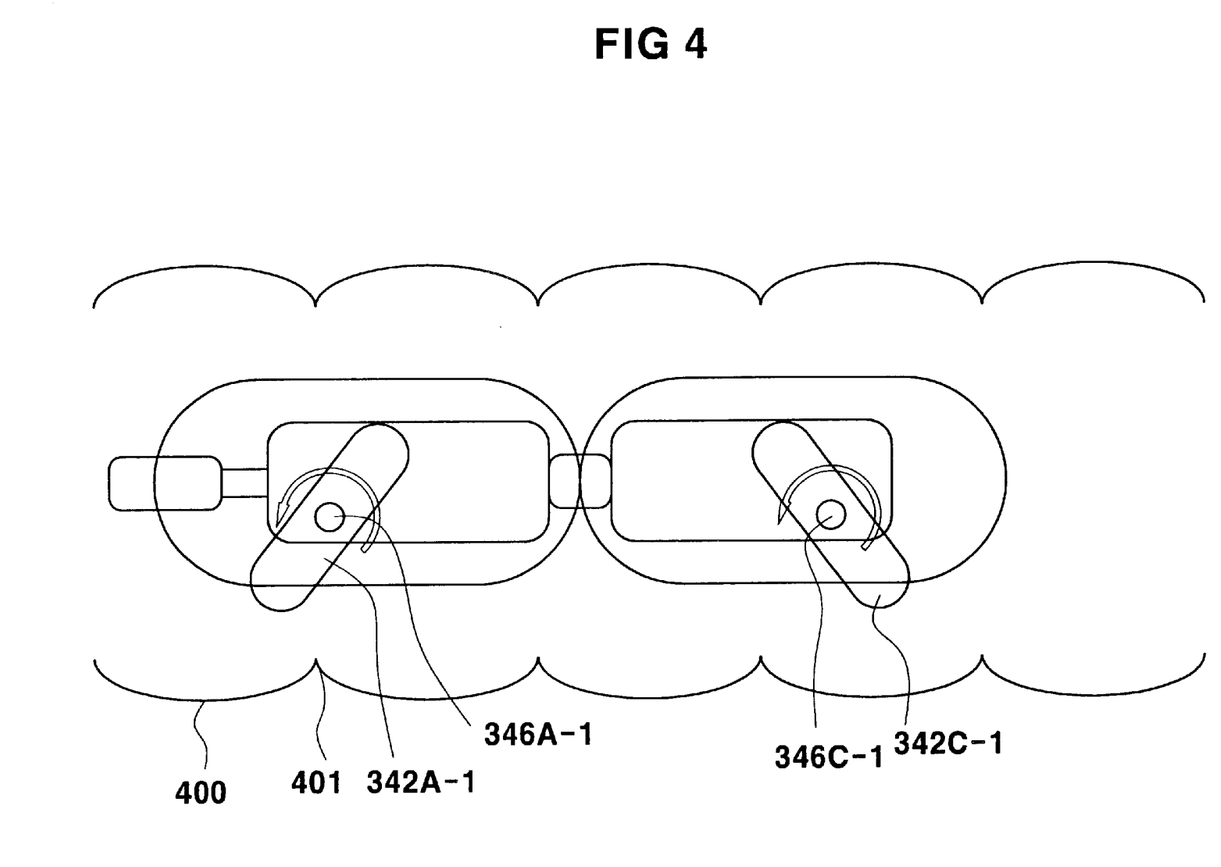
FIG. 4 is a side view explaining the driving unit of the micro-robot for colonoscope with motor locomotion in accordance with the present invention.

FIG. 4 is a side view for explaining the driving unit of the micro-robot for colonoscope with motor locomotion in accordance with the present invention.

As shown in the drawing, the wheel 342A-1 in the front driving unit 300A is rotated with reference to a shaft 346A-1 by the driving force from the driving force transmission unit 341A. Similarly, the wheel 342C-1 in the rear driving unit 300C is rotated with reference to a shaft 346C-1 by the driving force from the driving force transmission unit 341C.

Figure 5A:
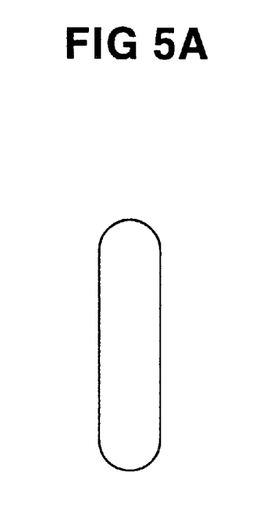
FIG. 5A is a sectional view of illustrating a first embodiment of the wheels of the driving unit of the micro-robot for colonoscope with motor locomotion in accordance with the present invention.
Figure 5B:
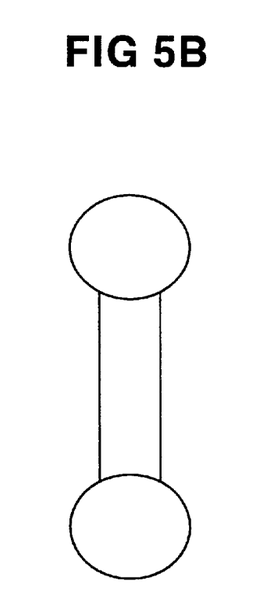
FIG. 5B is a sectional view of illustrating a second embodiment of the wheels of the driving unit of the micro-robot for colonoscope with motor locomotion in accordance with the present invention.

As shown in FIG. 5A and FIG. 5B, both ends of the wheels are embodied by a hemispherical shape or spherical shape, thereby the micro-robot 300 can freely move the interior of the colon without causing any damages thereto, even though micro-robot meets haustral folds 401 or a very angulated colon 400.

In FIG. 4, even though we explained the principle that each wheel of the front and the rear driving units rotates and advances in the colon such as the haustral folds 401, we can easily appreciate that the front and the rear driving units have two wheels at both sides to balance the micro-robot 300 and to effectively move in the colon without rotating at the same region. Also, the interval between the wheels of the front driving unit 300A and the rear driving unit 300C is determined by considering the distances between the haustral folds so as to easily move over the haustral folds.

We will now explain the operation of the micro-robot constructed above with reference to the following drawings.

Figure 6A:
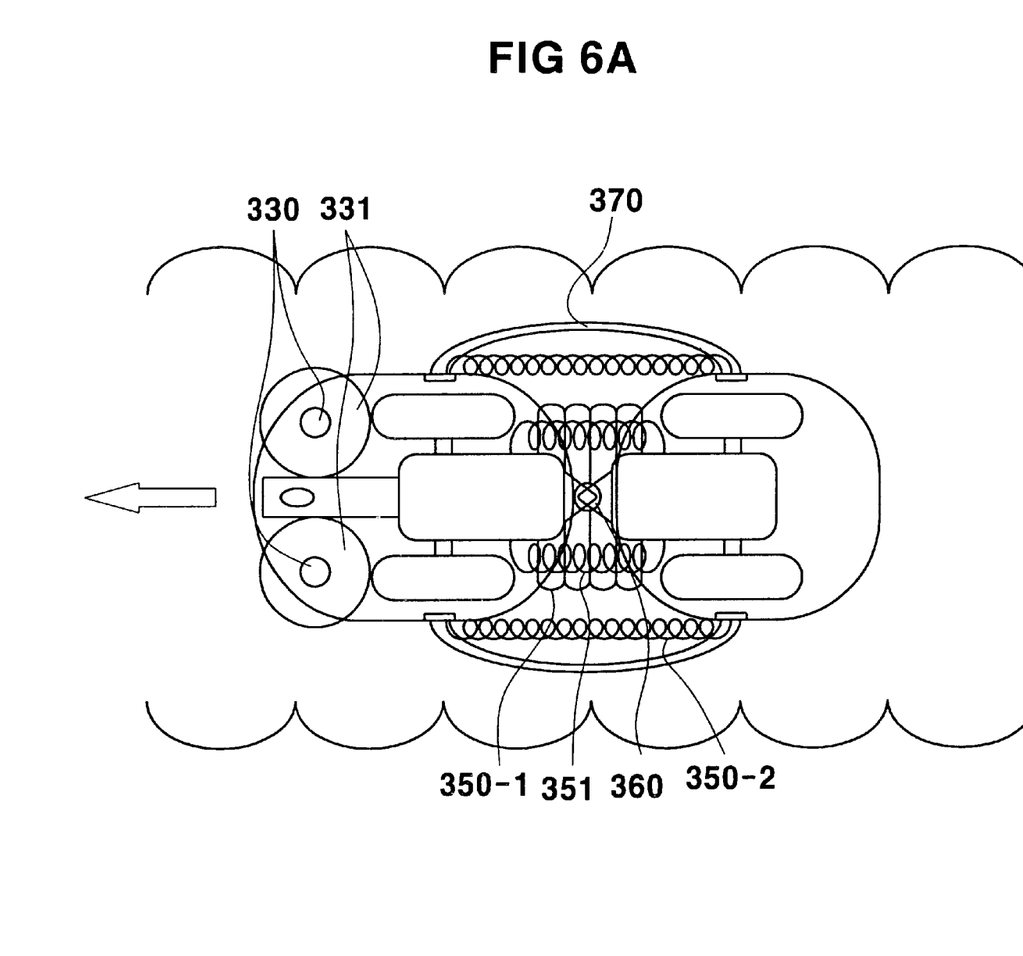
FIG. 6A is a perspective view for explaining the advancing procedure of the micro-robot for colonoscope with motor locomotion in accordance with the present invention.

FIG. 6A is a perspective view for explaining the advancing procedure of the micro-robot for colonoscope with motor locomotion in accordance with the present invention.

When the controlling unit 200 transmits a forward control signal to the micro-robot 300, then the micro-robot 300 advances in the colon.

Figure 6B:
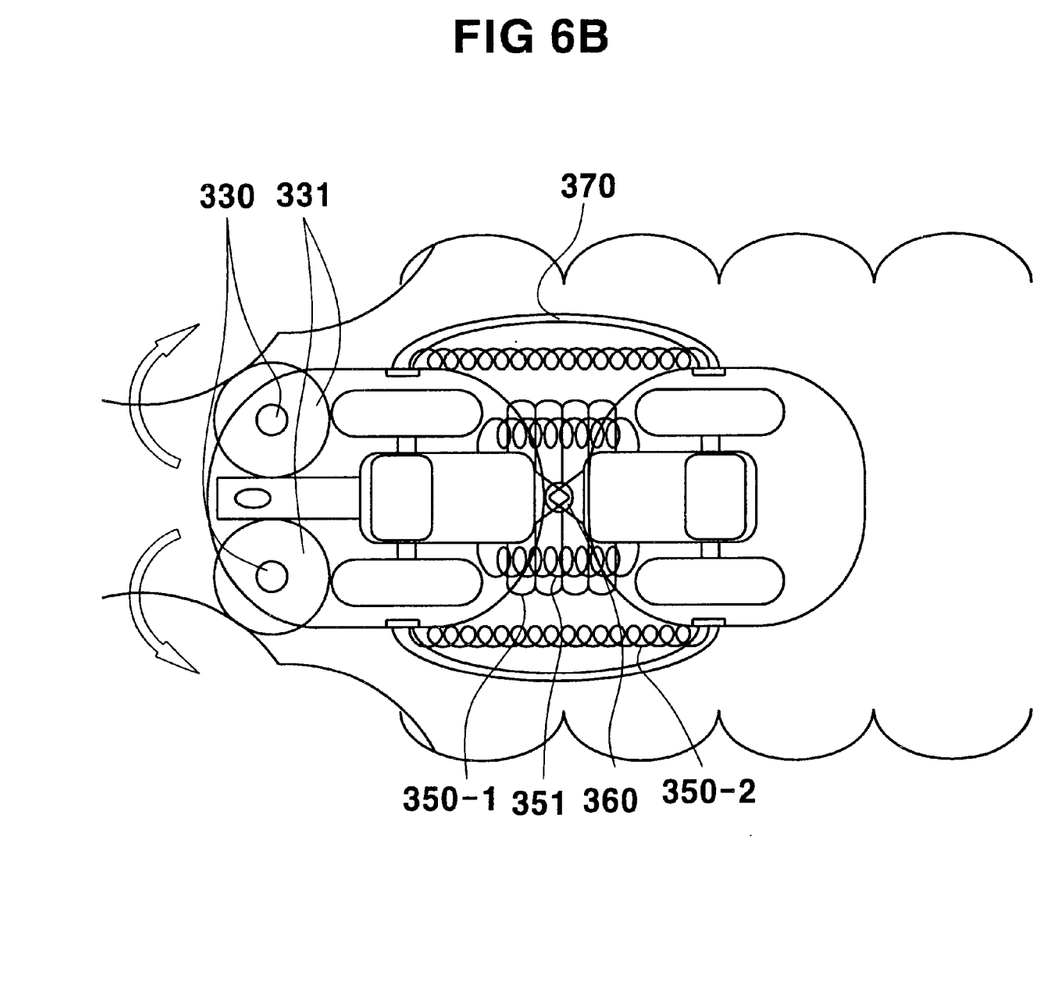
FIG. 6B is a perspective view for explaining the movement procedure of the micro-robot for colonoscope with motor locomotion in a narrow region of the colon in accordance with the present invention.

FIG. 6B is a perspective view for explaining the movement procedure of the micro-robot for colonoscope with motor locomotion in a narrow region of the colon in accordance with the present invention.

As shown in the drawing, when the tactile sensors 330 detect a pressure or force of the narrow region (or wall) of the colon as the micro-robot 300 is advancing and transmit a signal corresponding to the pressure or force to the controlling unit 200 via a wire 301, then the controlling unit 200 regulates the driving force lest the micro-robot 300 should inflict any damage to the inner wall of colon. When the micro-robot 300 is moved forward by the driving force of the motors, the passive steering units 331 widen the narrow region of the colon and reduce the frictional force between the micro-robot and the walls. Therefore, the micro-robot 300 can smoothly and easily pass the narrow region of the colon. Here, the tactile sensors 330 detect the magnitude of the force or pressure of the region of the colon and make the controlling unit 200 generate a signal transmitted to the micro-robot 300, thereby the micro-robot 300 overcomes the force or pressure of the region and advances to the region.

Meanwhile, if the micro-robot 300 is to be moved backward, the controlling unit 200 changes the electrical poles of the power supplied from the power supply 100 to the motor. Then the wheels start to reversely rotate and the micro-robot 300 moves backward. At the same time, if a user pulls the electrical wire connected to the micro-robot 300 backward, then the micro-robot 300 can easily move backward due to more effectively steering function and rotation of the motors. Due to this reason it is not necessary to add an additional passive steering unit to the rear driving unit 300C.

Figure 7:
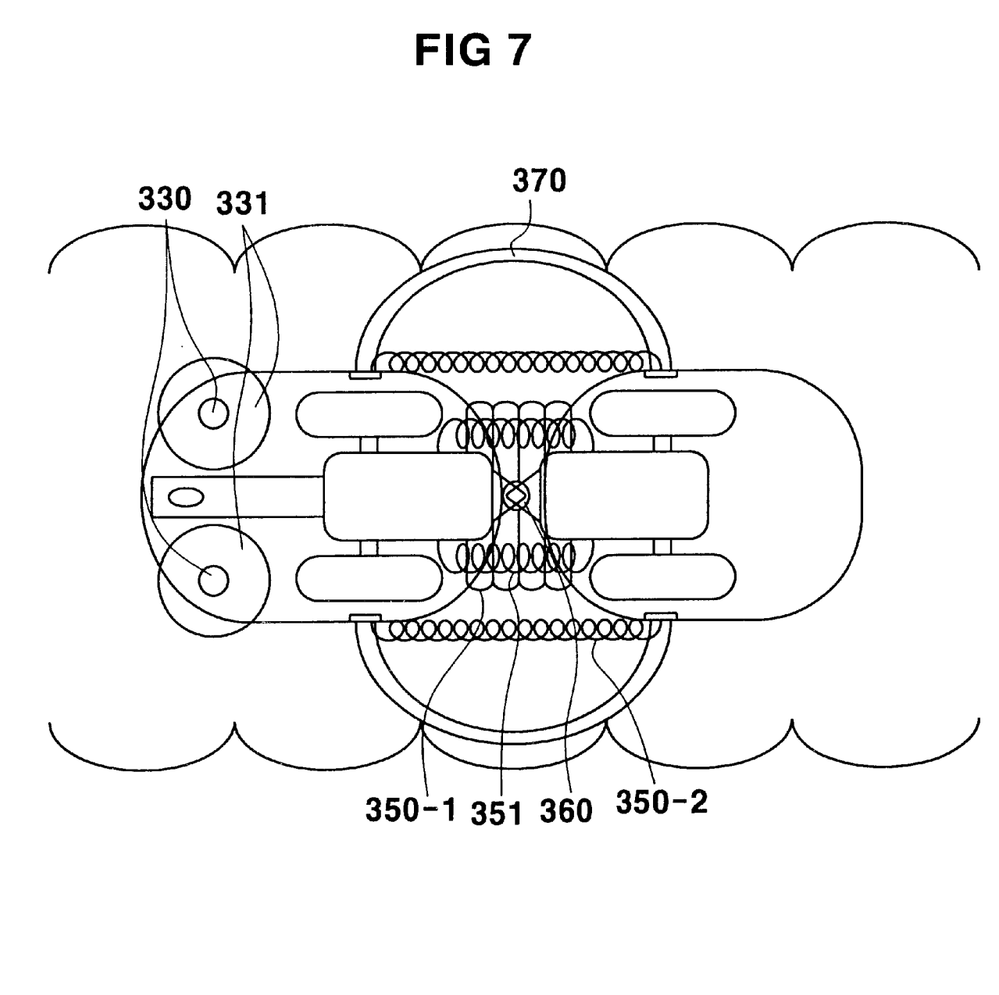
FIG. 7 is a perspective view explaining the procedure to fix the micro-robot for colonoscope with motor locomotion to the inner walls of the colon in accordance with the present invention.

FIG. 7 is a perspective view for explaining the procedure to fix the micro-robot for colonoscope with motor locomotion to the walls in accordance with the present invention.

As shown in the drawing, to obtain the more detail information of the interior of the colon, the fixing linear actuators 350-2 can fix the micro-robot 300 to the walls according to the control signal of the controlling unit 200. Here, the sliding units 343A-and 343C-1 are formed at the sides of the front driving unit 300A and the rear driving unit 300C as a type of groove. Therefore, the sliding units 343A-1 and 343C-1 can slidably connect with each end of the body supporting units 370 and help the body supporting unit 370 flexibly move therein. When the fixing linear actuators 350-2 reduce their own lengths, the body supporting unit 370 can change their own shapes. Here, the ends of the body supporting unit 370 slidably moves in the sliding units 343A-1 and 343C-1. As the outer surface of body support unit 370 bent by the fixing linear actuators 350-2 clings to the inner wall of the colon so does the micro-robot 300.

Figure 8A:
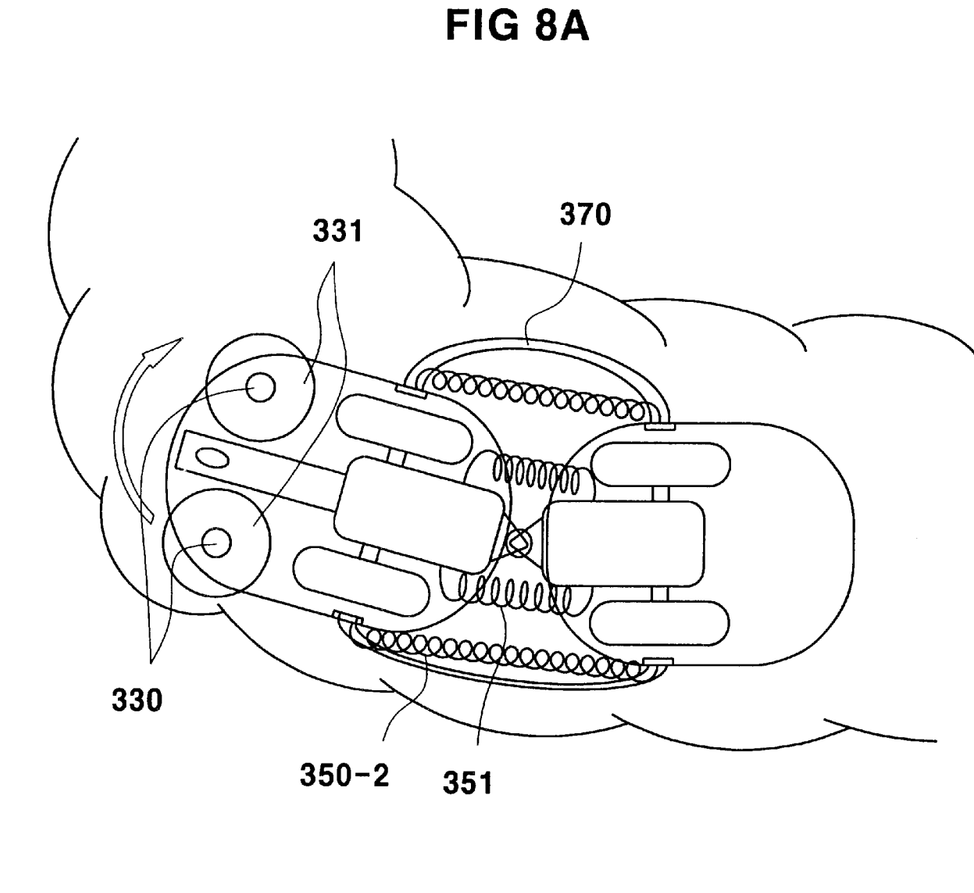
FIG. 8A is a perspective view for explaining the principle of steering the microrobot to the right of the advancing direction according to the control of the steering unit of FIG. 3.
Figure 8B:
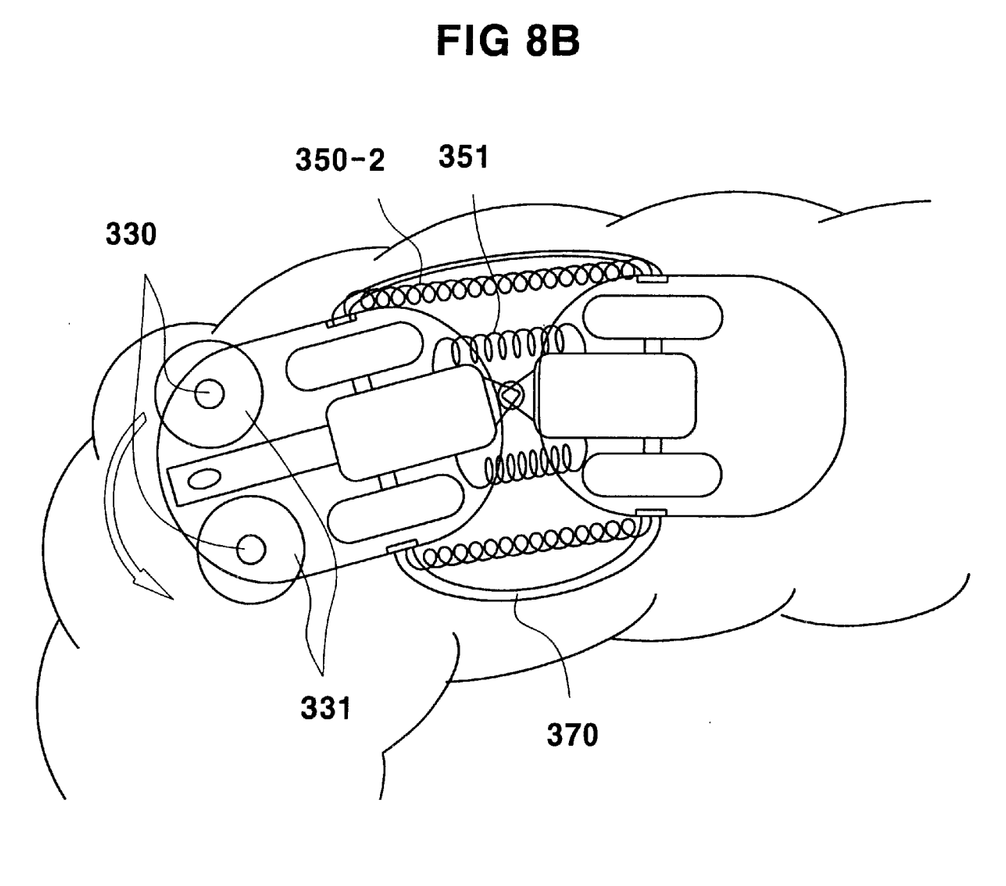
FIG. 8B is a perspective view for explaining the principle of steering the microrobot to the left of the advancing direction according to the control of the steering unit of FIG. 3.

FIGS. 8A and 8B are perspective views for explaining the principle of steering the micro-robot to the right and the left of the advancing direction according to the control of the steering unit of FIG. 3, respectively.

As shown in the drawings, the micro-robot 300 steers and advances to the right or the left as the steering linear actuators 350-1 are extended or contracted. Namely, since the steering linear actuators 350-1 are embodied by length variation materials such as a pneumatic pressure cylinder or shape-memory alloy or polymer according to the conditions applied thereto such as electric power or air pressure, the steering linear actuators 350-1 can change their own lengths and steer the micro-robot 300.

Meanwhile, the springs 351 play a role to align the front and rear driving units in the straight line or maintain an equilibrium state between them if the steering driving units 350-1 did not operate.

Accordingly, the micro-robot for colonoscope with locomotion according to the first embodiment as shown in FIG. 1 or 2 can flexibly move in the colon without causing any damages to the walls and obtain the precise information of them.

Figure 9:
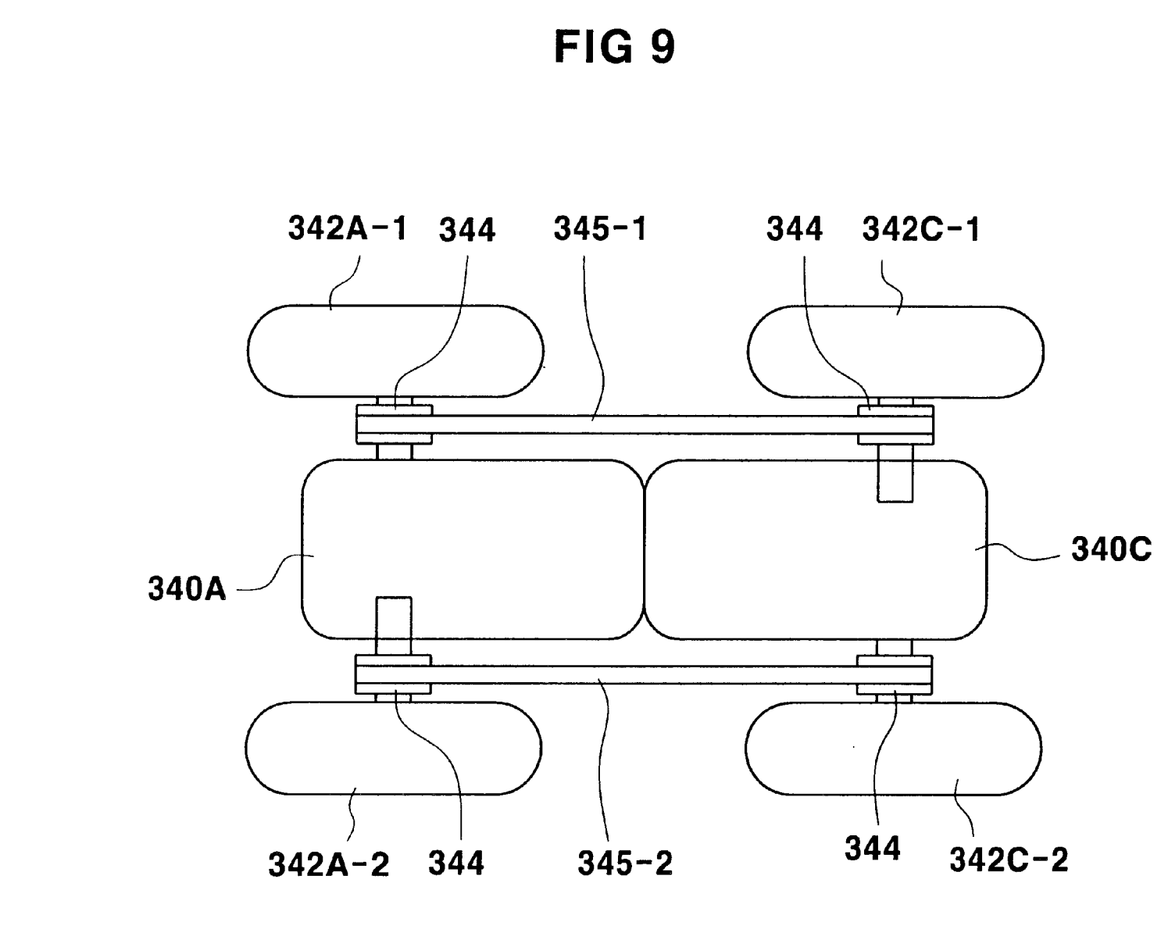
FIG. 9 is schematically illustrating a driving unit of a micro-robot for colonoscope with motor locomotion in accordance with the second embodiment of the present invention.

FIG. 9 is schematically illustrating a driving unit of a micro-robot for colonoscope with motor locomotion in accordance with the second embodiment of the present invention.

The driving unit comprises a front driving unit on which an information detecting unit (not illustrated) is installed, similar to the first embodiment of the present invention of FIG. 1 or 2, wherein the front driving units includes a front motor 340A to generate its own locomotion, front wheels 342A-1 and 342A-2 rotated by the locomotion, a driving force transmission unit to transmit the locomotion to the wheels 342A-1 and 342A-2; a rear driving unit with which the front driving unit (not illustrated) connected includes a rear motor 340C to generate its own locomotion according to the locomotion of the front driving unit, rear wheels 342C-1 and 342C-2 rotated by the locomotion, a driving force transmission unit to transmit the locomotion to the rear wheel 342C-1; and a steering unit which includes a plurality of pulleys 344 installed at the rotating axis, and timing belts 345 to wind the pulleys 344. Here each of belt winds the pulleys 344 of the front and the rear driving units at the right and the left sides of the micro-robot 300.

For example, the locomotion of the front motor 340A is transmitted to the rear wheel 342C-2 via the front wheel 342A-2 and the timing belt 345-2, and the locomotion of the rear motor 340C is transmitted to the front wheel 342A-1 through the rear wheel 342C-1 and the timing belt 345-1.

Therefore, the second embodiment according to the micro-robot for colonoscope with motor locomotion can control the wheels aligned at the respective side of the micro-robot and easily steer the micro-robot in the direction which is wanted.

Figure 10A:
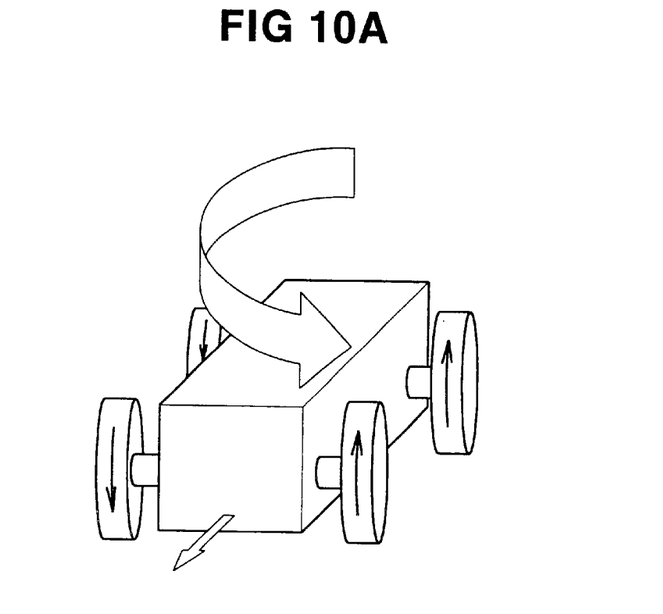
FIG. 10A is illustrating the principle of steering the micro-robot to the left of the advancing direction according to the control of the steering unit of FIG. 9.
Figure 10B:
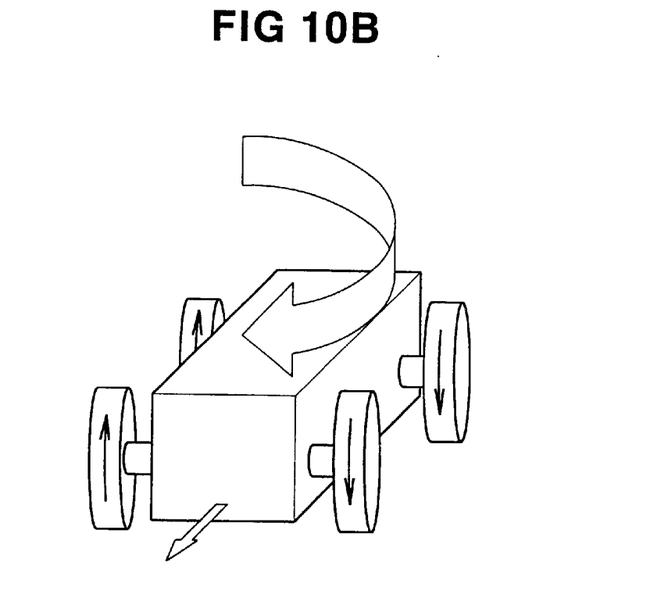
FIG. 10B is illustrating the principle of steering the micro-robot to the right of the advancing direction according to the control of the steering unit of FIG. 9.

FIGS. 10A and 10B are illustrating the principle of steering the micro-robot to the left and the right of the advancing direction according to the control of the steering unit drawn in FIG. 9, respectively.

As shown in the drawings, if the micro-robot 300 is to be moved to the left, the wheels aligned at the right side of the micro-robot rotate to the same direction as the advancing direction of the micro-robot and at the same time the wheels aligned at the left side rotate reversely. Similarly, the reverse mechanism above makes the microrobot to steer to the right.

As mentioned above, the micro-robot for colonoscope with motor locomotion and the system using the same in accordance with the present invention can easily, flexibly move forward and backward without causing any damages to the inner wall of the colon, and steer to the right and left by its own driving force generated by the motors or the variation of the length of the linear actuators. Also, the micro-robot and the system can obtain the precise information of the colon and relatively reduce the inspection or the examination time of the patient's colon, to reduce the pain which patients feel.

Although the present invention has been described in detail, it should be understood that various changes, substitutions, alterations, and modifications can be made herein without departing from the spirit and scope of the invention as defined by the appended claims.

What is claimed is:

1. A micro-robot colonoscope with motor locomotion, comprising:
 an information detecting unit for obtaining information of the interior of the colon and a driving unit for generating its own locomotion and moving the information detecting unit without causing any damages to the walls of the colon;
 said information detecting unit further comprises:
  a lighting emitting unit for emitting a light in the interior of the colon;
  a camera for taking images the interior as the lighting emitting unit illuminates; and
  a plurality of sensors for detecting pressure or force which the micro-robot applies to the interior of the colon.

2. The micro-robot according to claim 1, wherein said micro-robot further comprises:

a controlling unit for controlling the information detecting unit and the driving unit; and a power supplying unit for supplying power to the information detecting unit, the driving unit and the controlling unit.

3. A micro-robot colonoscope with motor locomotion, comprising:

an information detecting unit for obtaining information of the interior of the colon and a driving unit for generating its own locomotion and moving the information detecting unit without causing any damages to the walls of the colon;

said driving unit having a front driving unit for generating a first locomotion and moving in the colon according to the locomotion, which carries the information detecting unit thereon, a rear driving unit for generating a second locomotion and moving in the colon corresponding to the movement of the front driving unit, wherein the rear and front driving units are connected with each other in a predetermined distance, and a steering unit for relatively controlling the front and rear driving units and changing the advancing direction of the micro-robot, which is positioned between the front and rear driving units;

said front driving unit further comprises: a first motor for generating the first locomotion; a set of first wheels for rotating by the first locomotion; and a first driving force transmission unit for transmitting the first locomotion to the set of the first wheels.

4. The micro-robot according to claim 3 wherein said set of first wheels are rod-shape wheels having hemisphere or sphere at both the ends of each wheel.

5. The micro-robot according to claim 3 wherein said steering unit comprises:

a revolute joint for relatively rotating the front and rear driving units;

a plurality of steering linear actuators for controlling angles between the front and the rear driving units with respect to the revolute joint and thus helping steer the micro-robot; and a plurality of springs for maintaining the interval between the front and rear driving units and aligning the front and rear driving units in a straight line, provided that the linear actuators do not operate.

6. The micro-robot according to claim 5, wherein said steering linear actuators comprise a pneumatic pressure cylinder operated by air pressure or shape memory alloy and polymer varying its length according to the variation of the supplied power.

7. The micro-robot according to, claim 3 wherein said micro-robot further comprises a body supporting unit for fixing the micro-robot on the inner wall of colon, wherein said body supporting unit comprising:

a plurality of supporters for fixing the micro-robot on the inner wall of colon; and a plurality of fixing linear actuators for fixing the supporters to the inner wall of colon.

8. The micro-robot according to claim 7 wherein said fixing linear actuators comprise a pneumatic pressure cylinder operated by air pressure or shape memory alloy and polymer varying its length according to the variation of the supplied power.

9. A micro-robot colonoscope with motor locomotion, comprising:

an information detecting unit for obtaining information of the interior of the colon and a driving unit for generating its own locomotion and moving the information detecting unit without causing any damages to the walls of the colon;

said driving unit having a front driving unit for generating a first locomotion and moving in the colon according to the locomotion, which carries the information detecting unit thereon, a rear driving unit for generating a second locomotion and moving in the colon corresponding to the movement of the front driving unit, wherein the rear and front driving units are connected with each other in a predetermined distance, and a steering unit for relatively controlling the front and rear driving units and changing the advancing direction of the micro-robot, which is positioned between the front and rear driving units;

said rear driving unit further comprises: a motor for generating the second locomotion; a set of wheels for rotating by the second locomotion; and a driving force transmission unit for transmitting the second locomotion to the set of the wheels.

10. The micro-robot according to claim 9, wherein said set of the wheels are rod-shape wheels having hemisphere or sphere at both the ends of each wheel.

11. A micro-robot colonoscope with motor locomotion, comprising:

an information detecting unit for obtaining information of the interior of the colon and a driving unit for generating its own locomotion and moving the information detecting unit without causing any damages to the walls of the colon;

said driving unit having a front driving unit for generating a first locomotion and moving in the colon according to the locomotion, which carries the information detecting unit thereon; a rear driving unit for generating a second locomotion and moving in the colon corresponding to the movement of the front driving unit; and a steering unit for connecting the front and rear driving units and steering the micro-robot;

said front driving unit further comprises: a motor for generating a locomotion; a plurality of wheels for carrying the front driving unit; and a third driving force transmission unit for transmitting the locomotion to one of is the wheels.

12. The micro-robot according to claim 11, wherein said wheels are rod-shape wheels having hemisphere or sphere at both the ends of each wheel.

13. The micro-robot according to claim 11, wherein said steering unit comprises:

a first timing belt for connecting the wheel with the rear driving unit and transmitting the locomotion of the motor to the wheel and the rear driving unit; and a set of first pulleys for being wound by the first timing belt, which are installed at the axis where the third wheel attached and the rear driving unit, respectively.

14. A micro-robot colonoscope with motor locomotion, comprising:

an information detecting unit for obtaining information of the interior of the colon and a driving unit for generating its own locomotion and moving the information detecting unit without causing any damages to the walls of the colon;

said driving unit having a front driving unit for generating a first locomotion and moving in the colon according to the locomotion, which carries the information detecting unit thereon: a rear driving unit for generating a second locomotion and moving in the colon corresponding to the movement of the front driving unit: and a steering unit for connecting the front and rear driving units and steering the micro-robot;

said rear driving unit further comprises: a motor for generating locomotion; a plurality of wheels for carrying the rear driving unit; and driving force transmission unit for transmitting the locomotion to one of the wheels.

15. The micro-robot according to claim 14, wherein said wheels are rod-shape wheels having hemisphere or sphere at both the ends of each wheel.

16. The micro-robot according to claim 14, wherein said steering unit comprises:

a timing belt for connecting the wheel with the front driving unit and transmitting the locomotion of the motor to the wheel and the front driving unit; and a set of pulleys for being wound by the timing belt, which are installed at the axis where the wheel attaches and the front driving unit, respectively.

17. A systsm for colonoscopy, the system comprising:

a micro-robot for obtaining information of the interior of a colon, wherein the micro-robot comprises:

an information detecting unit for obtaining information of the interior of the colon; and a driving unit for generating its own locomotion and moving the information detecting unit without causing any damages to walls of the colon, the driving unit including:

a front driving unit for generating a first locomotion and moving in the colon according to the locomotion, which carries the information detecting unit thereon;

a rear driving unit for generating a second locomotion and moving in the colon corresponding to the movement of the front driving unit, wherein the rear and front driving units are connected with each other at a predetermined distance; and a steering unit for relatively controlling the front and rear driving units and changing the advancing direction of the micro-robot, which is positioned between the front and rear driving units, wherein the front driving unit comprises: a first motor for generating the first locomotion, a set of first wheels for rotating by the first locomotion; and a first driving force transmission unit for transmitting the first locomotion to the set of the first wheels;

a controlling unit for controlling the micro-robot; and a power supplying unit for supplying power to the micro-robot and the controlling unit.

18. The system according to claim 11 wherein said steering unit comprises:

a revolute joint for relatively rotating the front driving unit and the rear driving unit;

a plurality of linear actuators for controlling angles between the front driving unit and the rear driving unit with respect to the revolute joint and steering the micro-robot; and a plurality of springs for maintaining the interval between the front and the rear driving unit and aligning the front and rear driving units in a straight line provided that the linear actuators do not operate.

19. The system according to claim 17, controlling unit comprises an executive program for controlling the front and rear driving units and the steering unit according to the detected signals from the information detecting unit, so that the micro-robot flexibly moves in the colon and obtains the information of the inner wall of colon.

* * * * *